(12) United States Patent
Noiseux

(10) Patent No.: US 6,520,587 B2
(45) Date of Patent: Feb. 18, 2003

(54) ELBOW REST DEVICE FOR DENTAL PROFESSIONALS

(75) Inventor: Lyne Noiseux, Beloeil (CA)

(73) Assignee: Akio, R, D&D, Beloeil (CA)

(*) Notice: Subject to any disclaimer, the term of this patent is extended or adjusted under 35 U.S.C. 154(b) by 0 days.

(21) Appl. No.: 09/783,789

(22) Filed: Feb. 15, 2001

(65) Prior Publication Data

US 2002/0109387 A1 Aug. 15, 2002

(51) Int. Cl.[7] ................................................ A47C 7/54
(52) U.S. Cl. ............. 297/411.37; 297/173; 297/411.35; 297/411.39
(58) Field of Search ........................... 297/173, 188.21, 297/405, 411.35, 411.37, 411.38

(56) References Cited

U.S. PATENT DOCUMENTS

| | | | |
|---|---|---|---|
| 663,132 A | * 12/1900 | Ritter | 297/411.36 |
| 2,985,226 A | * 5/1961 | Mauer et al. | 297/395 |
| 3,063,752 A | * 11/1962 | Moore | 297/411.1 |
| 4,025,112 A | 5/1977 | Hale | |
| 4,031,576 A | 6/1977 | Epstein | |
| 4,277,102 A | * 7/1981 | Aaras et al. | 297/411.36 |
| 4,400,033 A | 8/1983 | Pietsch | |
| 4,411,471 A | 10/1983 | Ponzellini | |
| 4,565,409 A | * 1/1986 | Hollonbeck et al. | 297/411.1 |
| 4,822,103 A | 4/1989 | Stenvall | |
| 4,997,054 A | 3/1991 | Denny et al. | |
| 5,104,191 A | 4/1992 | Tame | |
| 5,342,006 A | 8/1994 | Tice | |
| 5,369,805 A | 12/1994 | Bergsten et al. | |
| 5,385,322 A | 1/1995 | Kim et al. | |
| 5,407,249 A | * 4/1995 | Bonutti | 297/411.35 |
| 5,536,070 A | 7/1996 | Lemmen | |
| 5,605,311 A | 2/1997 | McGrath et al. | |
| 5,755,650 A | * 5/1998 | Urso | 482/138 |
| 5,851,054 A | 12/1998 | Bergsten et al. | |
| 5,884,975 A | * 3/1999 | Su | 297/411.35 |
| 5,884,976 A | 3/1999 | Breen et al. | |
| 5,893,607 A | * 4/1999 | Trimnell | 297/170 |
| 5,927,815 A | * 7/1999 | Nakamura et al. | 297/411.38 |
| 6,102,344 A | * 8/2000 | Kasvin et al. | 248/118 |
| 6,220,556 B1 | * 4/2001 | Sohrt et al. | |

FOREIGN PATENT DOCUMENTS

| | | | |
|---|---|---|---|
| JP | 2001-169969 A | * | 6/2001 |
| WO | WO 9839995 | | 9/1998 |
| WO | WO 9904678 | | 2/1999 |
| WO | WO 9943237 | | 9/1999 |

* cited by examiner

Primary Examiner—Peter M. Cuomo
Assistant Examiner—Joseph Edell
(74) Attorney, Agent, or Firm—Collard & Roe, P.C.

(57) ABSTRACT

The present invention proposes an elbow rest device for use in the field of dentistry. The elbow rest device is connectable to an object. The device has a pad for supporting a user's elbow, an elongated member having an upper portion and a lower portion, the upper portion being coupled to the pad. The device further has a pivot mechanism for allowing the elongated member to be movable in a plane defined by a cone-like motion. The pivot mechanism is coupled to the lower portion of the elongated member. Finally, the device has a connecting assembly for connecting the elongated member to the object.

27 Claims, 7 Drawing Sheets

ELBOW REST DEVICE FOR DENTAL PROFESSIONALS

FIELD OF THE INVENTION

The present invention relates to an improved elbow rest device connectable to an object, preferably a chair.

BACKGROUND OF THE INVENTION

It is now a fact that in the field of dental hygiene, an increasing number of dental hygienists have developed pathologies that cause them to be absent from work for long periods of time, and making it difficult for them to return to work. Hygienist's work involves extended static muscular efforts in the neck and pectoral girdle, combined with recurrent dynamic movements of the wrist, fingers and arms, associated with physically difficult procedures. These drawbacks of their work have caused an increase of musculoskeletal injuries in the workplace.

Musculoskeletal pain (MS) is reported in people, like dental hygiene professionals, who during the course of their work, have prolonged exposure to static or repetitive arm movement. Therefore, hygienists are a classical group having high risk to be affected by MS pain.

A number of studies have been conducted on the MS problems experienced by dental hygienists and dentists. Symptoms may only appear after several years of practice, but seem to get worse after 10 years. According to Osborn et al. (Musculoskeletal Pain Among Minnesota Dental Hygienists, Journal of Dental Hygiene, March–April, 1990, p. 132–138), 68% of hygienists have experienced MS pain in the past year, and for nearly one-third of them, this pain affects their professional life. MS pain is more common among hygienists than among dentists because of their scaling activities.

They are few strategies that have been proposed in the literature to solve these problems. Some authors have suggested approaches relating mainly to postural hygiene. Others suggested some equipment changes. For instance, Oberg (Ergonomic Evaluation and Construction of a Reference Workplace in Dental Hygiene: A Case Study, Journal of Dental Hygiene, Vol. 67, no 5, July–August 1993, p. 262–267) tested a chair and armrest attached to the back of the patient's chair.

Despite every effort, the prior art devices do not adequately prevent MS injuries for dental hygienists. Indeed, there are still times when the hygienist's arms have to be maintained in an abduction position to work on certain quadrants of the mouth. Furthermore, even if the arms appear to be relaxed near the body, there is still static contraction at the level of the shoulder girdle to stabilize the arms and control the precision of the movement.

Therefore, there is still a need for a device that will support a hygienist's elbow while still offering mobility that does not obstruct the hygienist's work.

SUMMARY OF THE INVENTION

It is therefore an object of the present invention to provide an elbow rest device connectable to an object that will overcome these drawbacks.

In accordance with the present invention, that object is achieved with an elbow rest device connectable to an object having a portion lying in a vertical plane and a base. The device comprises a pad for supporting a user's elbow, an elongated member having an upper portion and a lower portion, the upper portion being coupled to the pad. The device further comprises a pivot mechanism for allowing the pad to be movable in a plane substantially transverse to the vertical plane of the object. The pivot mechanism is coupled to the lower portion of the elongated member. Finally, the device comprises a connecting assembly having a first section operatively connected to the object and a second section onto which the pivot mechanism is connected. The second section is positioned in proximity of the base of the object.

The present invention also proposes to provide a chair generally for use by dental professionals. The chair comprises a seat, a vertical support frame member for supporting the seat, the frame member being secured at its bottom end to a base and an elbow rest device as defined above.

An elbow rest device according to the present invention gives good mobility to the arms and hands of the hygienist as well as good support for the arms and shoulders resulting that such device provides increased freedom of movement in order to relieving the shoulder and neck muscles in an efficient way.

BRIEF DESCRIPTION OF THE DRAWINGS

The present invention and its advantages will be more easily understood after reading the following non-restrictive description of preferred embodiments thereof, made with reference to the following drawings wherein.

DESCRIPTION OF A PREFERRED EMBODIMENT

The present invention is directed to an elbow rest device (10) connectable to an object, which is preferably a chair. It will be understood that while the elbow rest device (10) according to the present invention may be used in a number of work environments. Such work environments may be those involving precision apparatuses like a microscope, or demanding skilled hand-work like textile manufacturing, surgery or cosmetic treatments. However, a particular advantageous work environment in which the present invention may find application is in the field of dentistry. Consequently, the present invention is also directed to a chair (12) generally for use by dental professionals. The chair (12) is of the type which comprises a seat (62), a vertical support frame member (64) for supporting the seat (62), the frame member (64) being secured at its bottom end to a base (66), and an elbow rest device (10) connectable to the seat (62). Such an elbow rest device (10) will be described in detail herein below.

Figure 1:
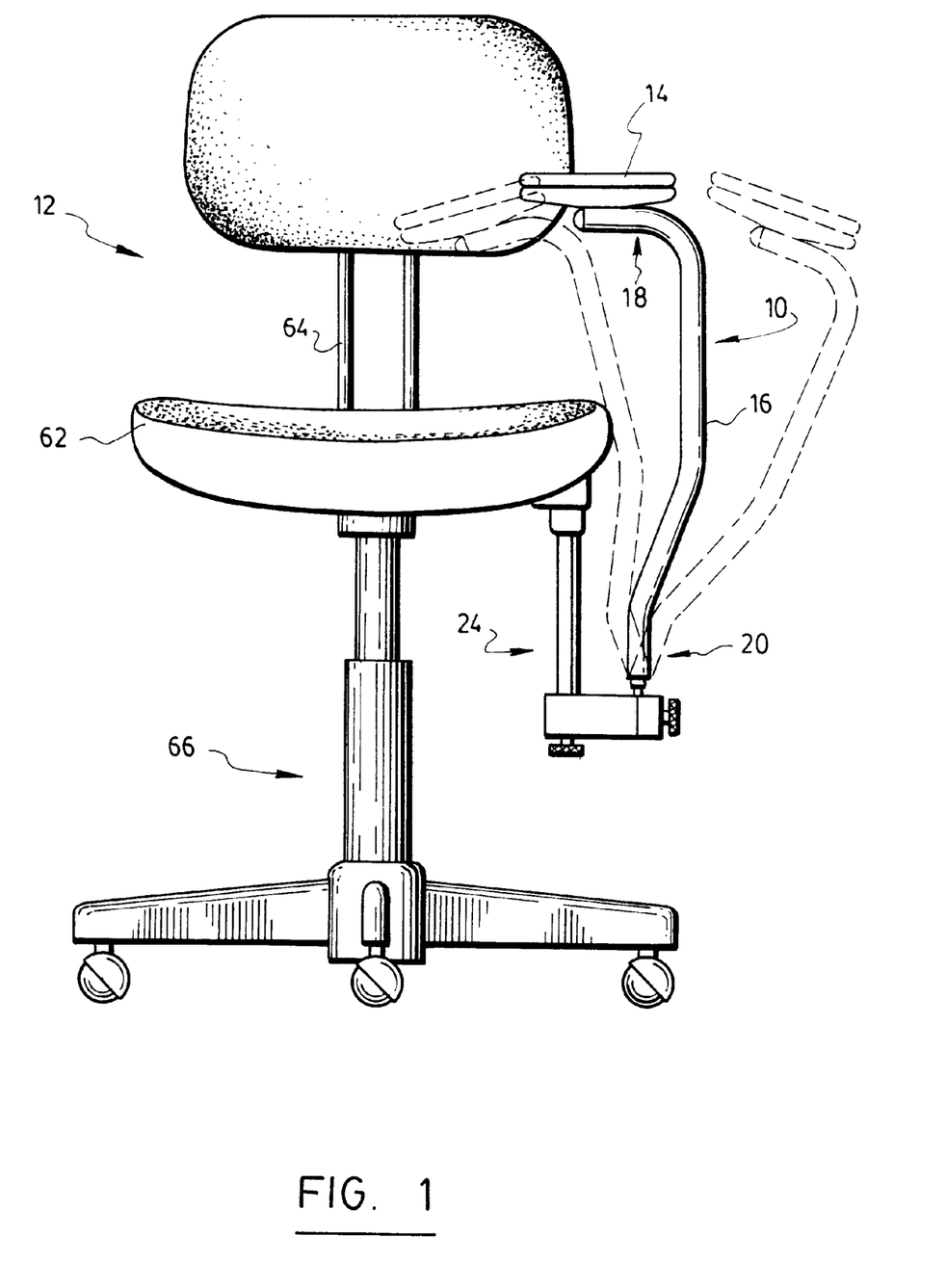
FIG. 1 is a front view of a chair equipped with an elbow rest device according to a preferred embodiment of the invention.

Therefore, depending of the work environment, one or two elbow rest devices (10) may be disposed on a chair (12). As shown in FIG. 1, a chair (12) is equipped with one elbow rest device (10) and such chair (12) may be particularly useful for any kind of manufacturing environment involving fine hand work. As can be appreciated, such chair (12) may be equipped with an elbow rest device (10) for either a left-handed or a right-handed user.

Figure 5:
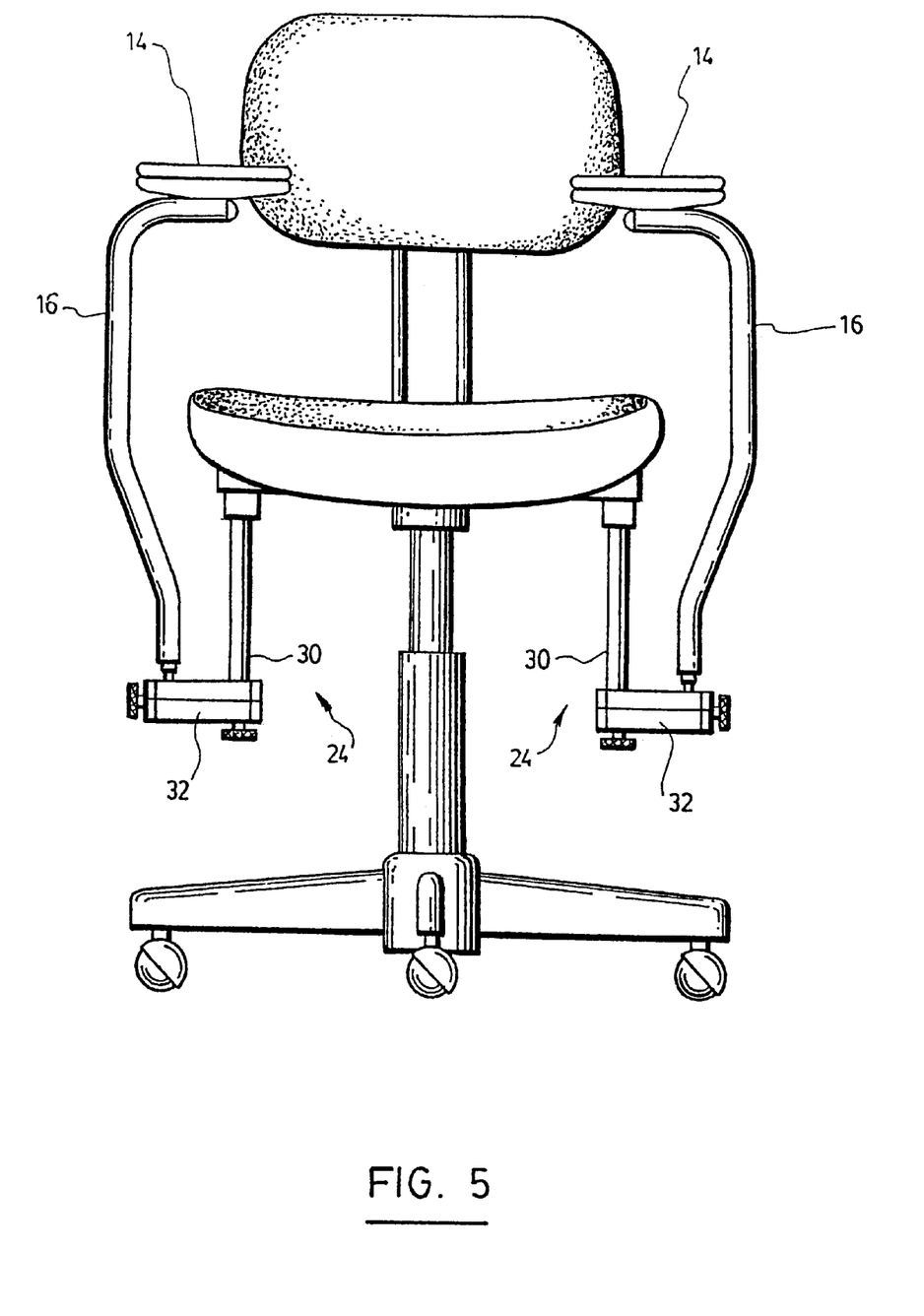
FIG. 5 is a front view of a chair equipped with two devices of FIG. 1, and showing a connecting assembly according to a preferred embodiment of the invention.
Figure 6:
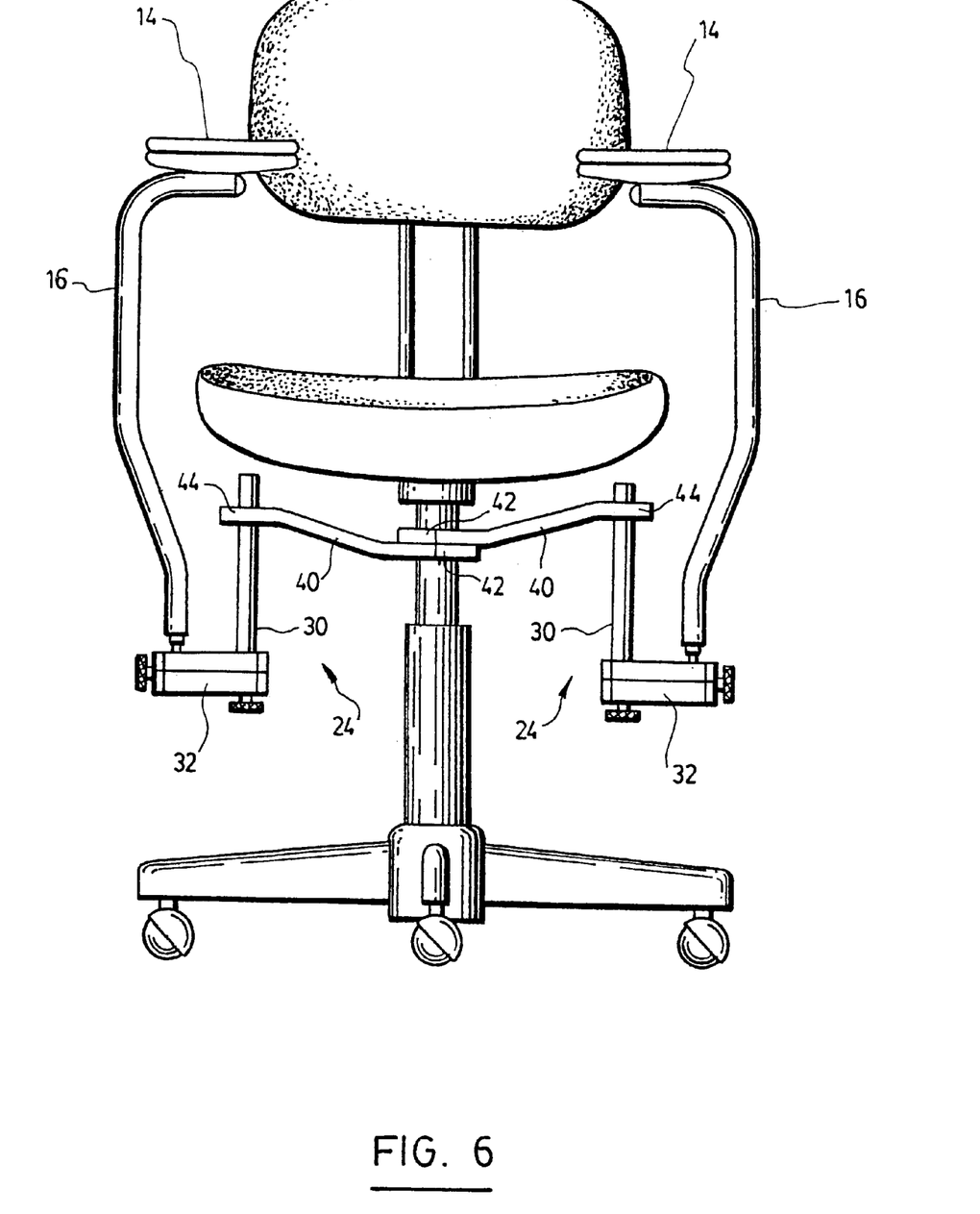
FIG. 6 is a front view of a chair equipped with two devices of FIG. 1, and showing a connecting assembly according to another preferred embodiment of the invention.

However, in the field of dentistry, it is a fact that a number of elements affect the working positions of dentists and hygienists. Therefore, a chair (12) equipped with two elbow rest devices (10) instead of one may be preferable in order to reduce the postural constraints which they are facing while treating a patient. Examples of such chairs (12) are shown in FIGS. 5 and 6.

Figure 2:
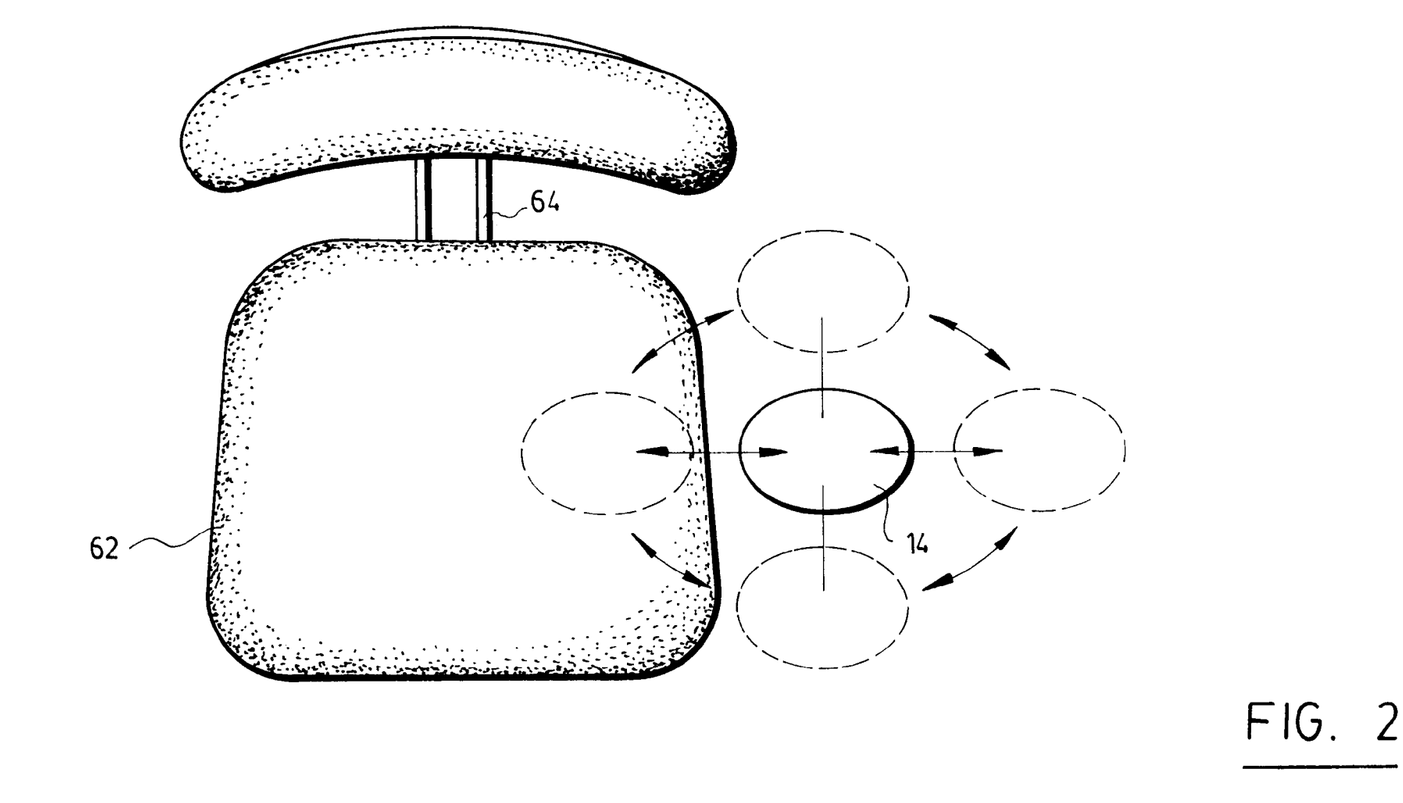
FIG. 2 is a top view of the chair of FIG. 1, showing the pivotal movement of the elbow rest device.

Now referring back to FIG. 1, the elbow rest device (10) according to a preferred embodiment of the invention comprises a pad (14) for supporting a user's elbow, an elongated member (16) having an upper portion (18) and a lower portion (20), a pivot mechanism (22) for allowing the elongated member (16) to be movable in a plane defined by a clone-like motion (see also FIG. 2). The elbow rest device (10) further comprises a connecting assembly (24) for connecting the elongated member (16) to the chair (12).

As indicated by the arrows in FIG. 2, the pivot mechanism (22) allows the elongated member (16) to be pivotable around its point of pivotal connection. In conjunction with the pivot mechanism (22), and in order to provide an optimal movement of the elongated member (16) of the elbow rest device (10), the elongated member (16) is preferably curved in shape. Its exact curvature will depend on the object or chair on which the elbow rest device (10) is connected to. Therefore, in the case that the elbow rest device (10) is connected to a chair, the elongated member (16) may have a shape or a profile similar to a "question mark" as illustrated in the accompanying drawings. This particular shape or any other similar shapes will provide greater movement of the elbow rest device (10). This will thus facilitate the adoption of new working methods by dental hygienists.

Figure 3:
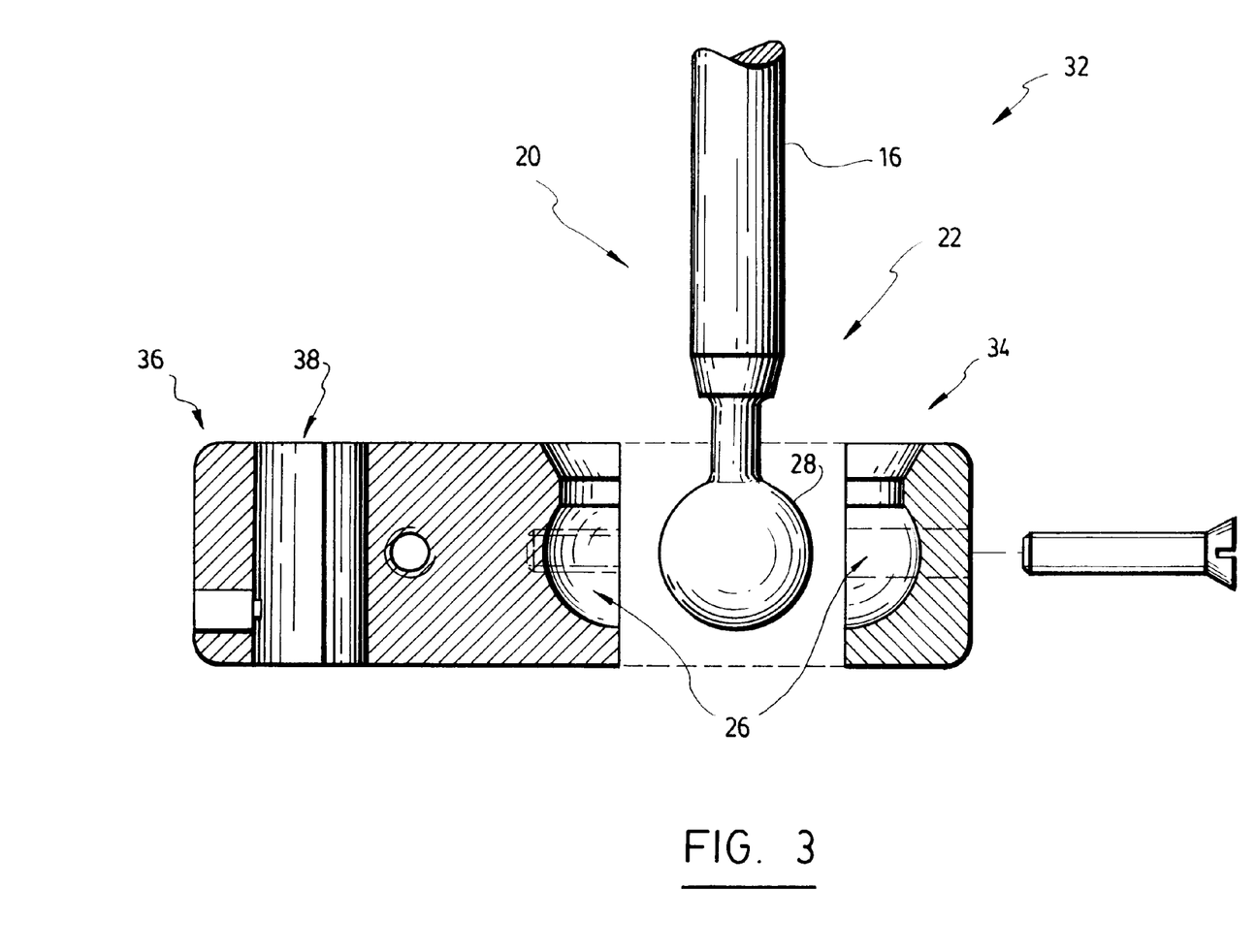
FIG. 3 is a cross-sectional view of a base of the connecting assembly, illustrating a pivot mechanism.

Viewing FIG. 1 in conjunction with FIG. 3, the pad (14) is coupled to the upper portion (18) of the elongated member (16) while the pivot mechanism (22) is coupled to the lower portion (20) of the elongated member (16). The coupling of the pad (14) to the upper portion (18) of the elongated member (16) is achieved with any fastening means known to one skilled in the art. The pad (14) may be permanently or removably coupled to the upper portion (18) of the elongated member (16).

Moreover, the pad (14) on which the user, such as a hygienist, is resting his/her elbow, is preferably cushioned and made of a gel-like material for maximizing comfort and reducing the transmission of vibrations from the tools used. Since the hygienist's elbow is somewhat moulded into the gel-like material, this helps to follow the hygienist's movements.

It will be understood that the precise pivot mechanism may vary depending to the work environment and the desired application. As can be appreciated and better seen in FIG. 3, the present invention preferably contemplates of employing as a pivot mechanism (22), a pivot joint (22). Such pivot joint (22) is made from the combination of a socket (26) and a ball structure (28) designed to snuggly fit within the socket (26). The ball structure (28) of the pivot joint (22) is coupled to the lower portion (20) of the elongated member (16). The coupling of the ball structure (28) to the lower portion (20) of the elongated member (16) is achieved with any fastening means known to one skilled in the art. Alternatively, the ball structure (28) may be permanently coupled to the lower portion (20) of the elongated member (16), in such a way that the ball structure (28) and the elongated member (16) are provided as one unit.

Figure 4:
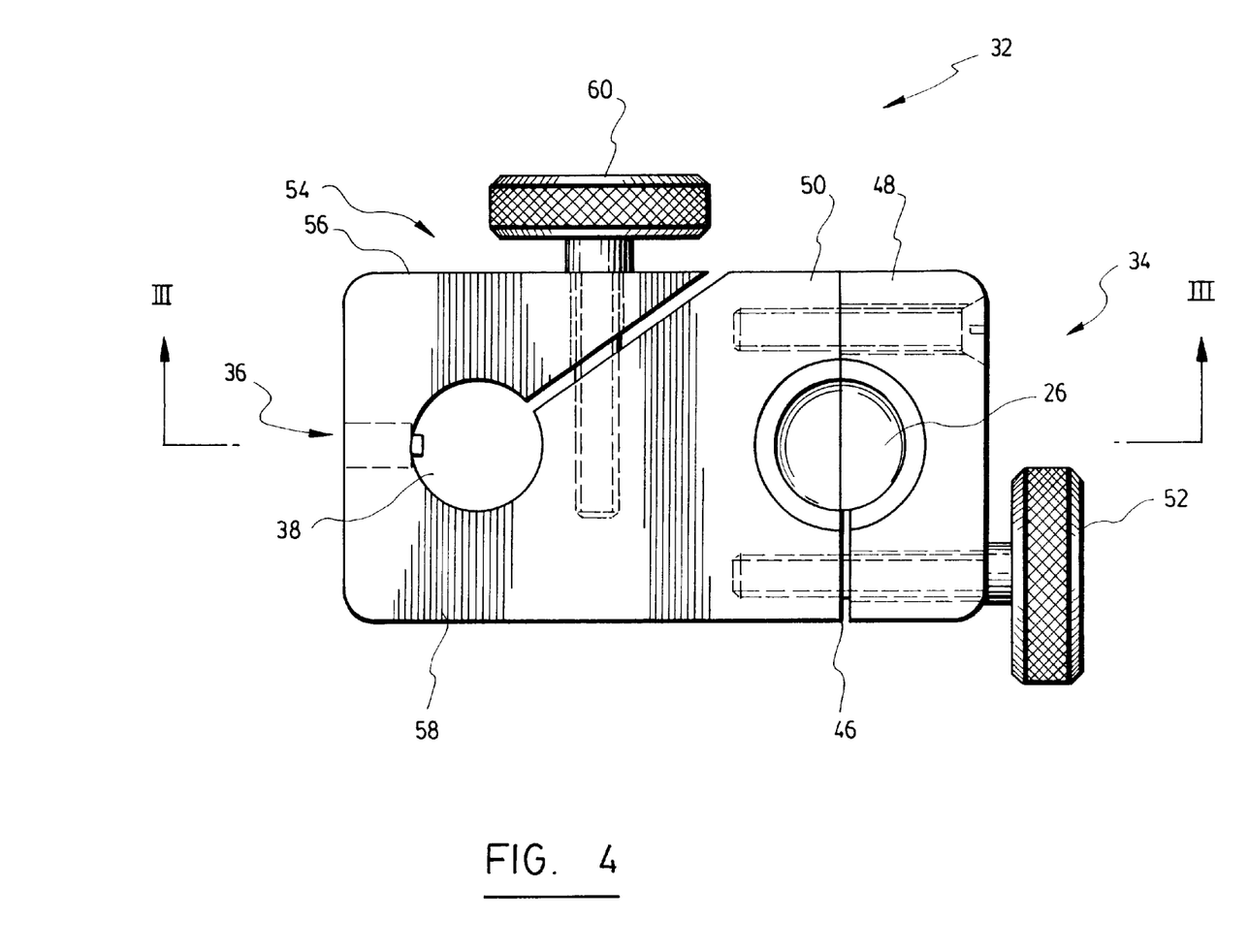
FIG. 4 is a top view of the base of FIG. 3.

According to a preferred embodiment of the invention and as better seen in conjunction with FIGS. 3 to 5, the connecting assembly (24) comprises a substantially vertically extending guide member (30) coupled to the chair (12) and a mounting base (32) having a first part (34) and a second part (36). The socket (26) of the pivot joint (22) is formed in the first part (34) of the mounting base (32) while the second part (36) is provided with a through-hole (38) for slidably connecting the guide member (30) so that the mounting base (32) is movable along the length of the guide member (30).

As can be appreciated by viewing FIG. 6 in conjunction with FIGS. 3 and 4, another preferred embodiment of the invention is illustrated. There, the connecting assembly (24) comprises a connecting bar (40) with a first extremity (42) and a second extremity (44). The first extremity (42) is connected to the chair (12). The connecting assembly (24) also comprises a substantially vertically extending guide member (30) coupled to the second extremity (44) of the bar (40) and a mounting base (32) having a first part (34) and a second part (36). The socket (26) of the pivot joint (22) is formed in the first part (34) of the mounting base (32) while the second part (36) is provided with a through-hole (38) for slidably connecting the guide member (30) so that the mounting base (32) is movable along the length of the guide member (30).

Since several hygienists or dentists may use the same chair, the guide member (30) may be graduated in order to provide quick and easy height adjustments.

Figure 7:
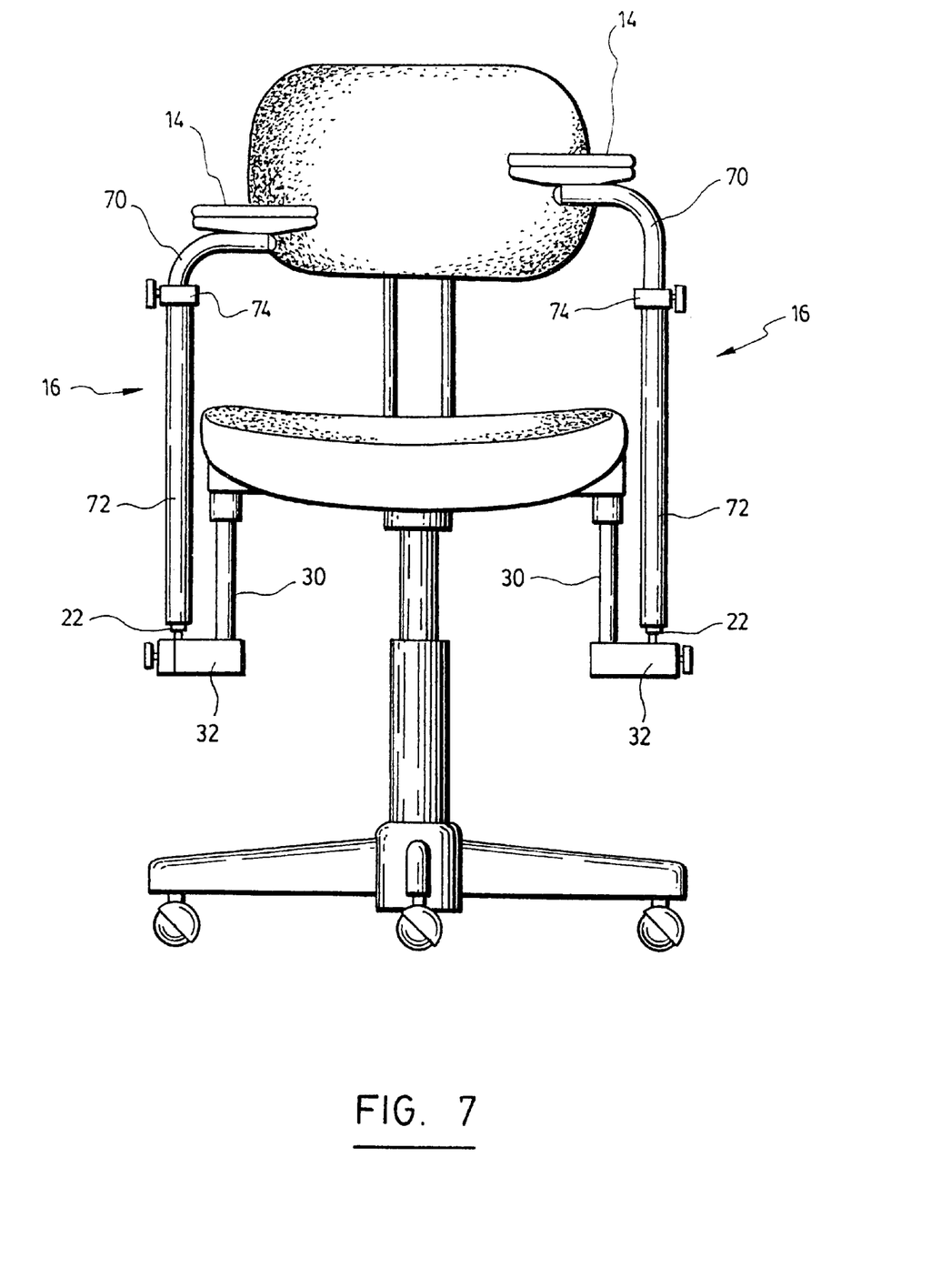
FIG. 7 is a front view of a chair equipped with two devices of FIG. 1, and showing an elongated member according to another preferred embodiment of the invention.

According to a preferred embodiment and as better seen in FIG. 7, the elongated member (16) is telescopic. In such a case, the mounting base (32) is preferably not movable along the length of the guide member (30). More specifically, the elongated member (16) comprises an outer tube (72) coupled at its bottom end to the pivot mechanism (22) and an inner tube (70) coupled at its upper end to the pad (14), the inner tube (70) being concentrically and slidably disposed within the outer tube (72). Therefore, a selected height of the inner tube may be increased or decreased depending of the user's choice. In order to maintain the selected position, fastening means such as a tightening screw (74) or any fastening means known to a person skilled in the field which is suitable for fastening the inner tube (72) and the outer tube (70) together will suffice.

Referring back to FIG. 4, the first part (34) of the mounting base (32) of the connecting assembly (24) comprises an adjustable clamp (46) for adjustably tightening the ball structure (28) within the socket (26) of the pivot joint (22), whereby the elongated member (16) is provided with more or less freedom of movement. The adjustable clamp (46) comprises a clamping component (48) and a receiving component (50), each component (48, 50) having a portion of the socket (26) of the pivot joint (22); and fastening means (52) for adjustably holding the clamping component (48) and the receiving component (50) together.

The second part (36) of the mounting base (32) is adaptable to being loosened by way of clamping means (54) in order to allow the mounting base (32) to move into a selected position along the length of the guide member (30). The clamping means (54) comprises a clamping element (56) and a receiving element (58) hingingly linked to the clamping element (56), each element (56, 58) having a portion of the trough-hole (38) of the second part (36) of the mounting base (32) and fastening means (60) for adjustably holding the clamping element (56) and the receiving element (58) together.

The above-mentioned fastening means (52, 60) are provided for securing the components (48, 50) or elements (56, 58) of the mounting base (32). Despite the fact that the present invention prefers employing screw-like fasteners as the fastening means (60), it will be understood that any other fastening means commonly known will suffice.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. An elbow rest device connectable to an object, said object having a portion lying in a horizontal plane and a base, the device comprising:
    a pad shaped and sized for supporting only a user's elbow;
    an elongated member having an upper portion and a lower portion, the upper portion being coupled to the pad;
    a pivot mechanism for allowing the pad to be movable in a plane substantially parallel to the horizontal plane of the object, the pivot mechanism being coupled to the lower portion of the elongated member; and
    a connecting assembly having a first section operatively connected to the object and a second section onto which the pivot mechanism is connected, the second section being positioned in proximity of the base of the object, said base being located at a distance from said portion of said object, so that said second section is closer to said base than to said portion of said object.

2. A device according to claim 1, wherein the pivot mechanism is a pivot joint made from the combination of a socket and a ball structure designed to snuggly fit within the socket, the ball structure being coupled to the lower portion of the elongated member.

3. A device according to claim 2, wherein:
    the first section of the connecting assembly comprises a guide member extending towards the base of the object; and wherein:
        the second section of the connecting assembly comprises a mounting base having a first part and a second part, the socket of the pivot joint being formed in the first part of the mounting base, the second part being provided with a through-hole for slidably connecting the guide member so that the mounting base is movable along the length of the guide member.

4. A device according to claim 3, wherein the first part of the mounting base of the connecting assembly comprises an adjustable clamp for adjustably tightening the ball structure within the socket of the pivot joint without locking the elongated member into a position in order to allow the elongated member to freely move to another position.

5. A device according to claim 4, wherein the adjustable clamp comprises:
    a clamping component and a receiving component, each component having a portion of the socket of the pivot joint; and
    fastening means for adjustably holding the clamping component and the receiving component together.

6. A device according to claim 5, wherein the second part of the mounting base is adaptable to being loosened by way of clamping means in order to allow the mounting base to move into a selected position along the length of the guide member.

7. A device according to claim 6, wherein the clamping means comprises:
    a clamping element and a receiving element hingingly linked to the clamping element, each element having a portion of the trough-hole of the second part of the mounting base; and
    fastening means for adjustably holding the clamping element and the receiving element together.

8. A device according to claim 2, wherein:
    the first section of the connecting assembly comprises:
        a connecting bar with a first extremity and a second extremity, said first extremity being connected to the object;
        a guide member coupled to the second extremity of the bar and extending towards the base of the object; and wherein
    the section of the connecting assembly comprises:
        a mounting base having a first part and a second part, the socket of the pivot joint being formed in the first part of the mounting base, the second part being provided with a through-hole for slidably connecting the guide member so that the mounting base is movable along the length of the guide member.

9. A device according to claim 2, wherein:
    the first section of the connecting assembly comprises a guide member extending towards the base of the object; and wherein:
        the second section of the connecting assembly comprises a mounting base having a first part and a second part, the socket of the pivot joint being formed in the first part of the mounting base, the second part being connected to the guide member.

10. A device according to claim 1, wherein the elongated member is telescopic.

11. A device according to claim 1, wherein the pad is cushioned.

12. A device according to claim 1, wherein the elongated member is curved in order to provide an optimal movement of the elongated member.

13. A device according to claim 1, wherein the object is a chair.

14. An elbow rest device according to claim 1, wherein placing said second section closer to said base than to said portion of said object results in an increased length of said elongated member, so that said pad travels in a plane that is substantially flat.

15. A chair generally for use by dental professionals, said chair having a portion lying in a vertical plane and comprising:
    a seat;
    a vertical support frame member for supporting the seat, said frame member being secured at a bottom end to a base; and
    an elbow rest device connectable to the chair; said device comprising:
        a pad shaped and sized for supporting only a user's elbow;
        an elongated member having an upper portion and a lower portion, the upper portion being coupled to the pad;
        a pivot mechanism for allowing the pad to be movable in a plane substantially transverse to the vertical plane of the chair, the pivot mechanism being coupled to the lower portion of the elongated member; and a connecting assembly having a first section operatively connected to the chair and a second section onto which the pivot mechanism is connected, the second section being positioned in proximity of the base of the chair and distanced from said seat.

16. A chair according to claim 15, wherein the pivot mechanism is a pivot joint made from the combination of a socket and a ball structure designed to snuggly fit within the socket, the ball structure being coupled to the lower portion of the elongated member.

17. A chair according to claim 16, wherein:

the first section of the connecting assembly comprises:
a connecting bar with a first extremity and a second extremity, said first extremity being connected to the chair;
a guide member coupled to the second extremity of the bar and extending towards the base of the chair; and wherein the second section of the connecting assembly comprises:
a mounting base having a first part and a second part, the socket of the pivot joint being formed in the first part of the mounting base, the second part being provided with a through-hole for slidably connecting the guide member so that the mounting base is movable along the length of the guide member.

18. A chair according to claim 16, wherein:

the first section of the connecting assembly comprises a guide member extending towards the base of the chair; and wherein:

the second section of the connecting assembly comprises a mounting base having a first part and a second part, the socket of the pivot joint being formed in the first part of the mounting base, the second part being provided with a through-hole for slidably connecting the guide member so that the mounting base is movable along the length of the guide member.

19. A chair according to claim 18, wherein the first part of the mounting base of the connecting assembly comprises an adjustable clamp for adjustably tightening the ball structure within the socket of the pivot joint without locking the elongated member into a position in order to allow the elongated member to freely move to another position.

20. A chair according to claim 19, wherein the adjustable clamp comprises:

a clamping component and a receiving component, each component having a portion of the socket of the pivot joint; and fastening means for adjustably holding the clamping component and the receiving component together.

21. A chair according to claim 20, wherein the second part of the mounting base is adaptable to being loosened by way of clamping means in order to allow the mounting base to move into a selected position along the length of the guide member.

22. A chair according to claim 21, wherein the clamping means comprises:

a clamping element and a receiving element hingingly linked to the clamping element, each element having a portion of the trough-hole of the second part of the mounting base; and fastening means for adjustably holding the clamping element and the receiving element together.

23. A chair according to claim 16, wherein:

the first section of the connecting assembly comprises a guide member extending towards the base of the chair; and wherein:

the second section of the connecting assembly comprises a mounting base having a first part and a second part, the socket of the pivot joint being formed in the first part of the mounting base, the second part being connected to the guide member.

24. A chair according to claim 15, wherein the pad is cushioned.

25. A chair according to claim 15, wherein the elongated member is curved in order to provide an optimal movement of the elongated member.

26. A chair according to claim 15, wherein the elongated member is telescopic.

27. A chair according to claim 15, wherein distancing said second section from said seat results in an increased length of said elongated member, so that said pad travels in a plane that is substantially flat.

* * * * *